(12) United States Patent
Riscalla (10) Patent No.: US 10,444,075 B1
(45) Date of Patent: *Oct. 15, 2019

(54) SYSTEMS AND METHODS FOR LOGGING TEMPERATURES OF FOOD PRODUCTS

(71) Applicant: Daniel Riscalla, Orange, CA (US)

(72) Inventor: Daniel Riscalla, Orange, CA (US)

(\*) Notice: Subject to any disclaimer, the term of this patent is extended or adjusted under 35 U.S.C. 154(b) by 0 days.

This patent is subject to a terminal disclaimer.

(21) Appl. No.: 15/979,353

(22) Filed: May 14, 2018

Related U.S. Application Data (63) Continuation of application No. 15/044,056, filed on Feb. 15, 2016, now Pat. No. 10,060,798.

(60) Provisional application No. 62/116,280, filed on Feb. 13, 2015.

(51) Int. Cl.
| | |
|---|---|
| *G01J 5/02* | (2006.01) |
| *H04W 4/70* | (2018.01) |
| *G01N 33/02* | (2006.01) |
| *G01J 5/10* | (2006.01) |
| *H04W 4/021* | (2018.01) |
| *G06Q 10/10* | (2012.01) |
| *H04L 29/08* | (2006.01) |
| *G06Q 30/00* | (2012.01) |
| *G06Q 50/12* | (2012.01) |
| *G06K 9/00* | (2006.01) |
| *H04N 5/225* | (2006.01) |
| *G06F 16/58* | (2019.01) |

(52) U.S. Cl.
CPC ............... *G01J 5/025* (2013.01); *G01J 5/10* (2013.01); *G01N 33/02* (2013.01); *G06F 16/5866* (2019.01); *G06K 9/00671* (2013.01); *G06Q 10/109* (2013.01); *G06Q 30/018* (2013.01); *G06Q 50/12* (2013.01); *H04L 67/18* (2013.01); *H04N 5/225* (2013.01); *H04W 4/021* (2013.01); *H04W 4/70* (2018.02)

(58) Field of Classification Search
None
See application file for complete search history.

(56) References Cited

U.S. PATENT DOCUMENTS 10,060,798 B1 \* 8/2018 Riscalla ................. H04W 4/70

\* cited by examiner

*Primary Examiner* — Michael Lebentritt
(74) *Attorney, Agent, or Firm* — William A. English; Vista IP Law Group LLP

(57) ABSTRACT

Systems and methods are provided for logging temperatures of food products using a temperature assembly including a housing and a temperature probe, e.g., an infrared probe, for acquiring a temperature of a food product, and a mobile electronic device including a camera, a communication interface for communicating with the temperature assembly, a processor configured to acquire a temperature reading from the temperature assembly and an image from the camera when the temperature reading is acquired, and memory for storing the temperature reading and image.

36 Claims, 9 Drawing Sheets

SYSTEMS AND METHODS FOR LOGGING TEMPERATURES OF FOOD PRODUCTS

RELATED APPLICATION DATA

The present application is a continuation of co-pending application Ser. No. 15/044,056, filed Feb. 15, 2016, which claims benefit of provisional application Ser. No. 62/116,280, filed Feb. 13, 2015, the entire disclosures of which are expressly incorporated by reference herein.

FIELD OF THE INVENTION

The present invention relates to systems and methods for measuring temperatures of food products, e.g., within a restaurant or other establishment where food products or ingredients are stored and/or used. More particularly, the present invention relates to a temperature sensing apparatus that may be coupled to and/or communicate with a mobile electronic device and to systems and methods for acquiring, logging, and/or maintaining temperature records for food products using such an apparatus.

BACKGROUND

Restaurants and other food service businesses generally capture temperatures of food products used by the businesses on a regular basis. For example, a restaurant that prepares food products from ingredients may acquire and maintain temperature information for ingredients stored at the restaurant, e.g., in a food preparation area where finished products are assembled or otherwise made from the ingredients. For example, a restaurant may establish a policy to acquire and log temperature data multiple times a day to ensure that the food products are stored within desired temperature ranges, e.g., for health and/or other safety reasons.

A thermometer may be used to acquire temperatures of individual food products, e.g., stored in a refrigerated or warmed condition for this purpose. For example, an infrared thermometer may be used to remotely acquire the temperature of food products, or a thermometer probe may be inserted into food products to acquire temperatures. The acquired temperatures may be manually logged, e.g., onto a form, and stored for later review and/or inspection by management, health inspectors, and/or other interested parties.

Such manual acquisition may risk error or deception on the part of the individuals acquiring and logging the temperatures. For example, the user may incorrectly read the thermometer, may enter the data incorrectly into the form, or may even enter false information.

Accordingly, systems and methods that facilitate and/or ensure more accurately acquiring, logging, and/or maintaining temperature records for food products would be useful.

SUMMARY

The present invention is directed to systems and methods for measuring temperatures of food products, e.g., within a restaurant or other establishment where food products or ingredients are stored and/or used. More particularly, the present invention is directed to a temperature sensing apparatus that may be coupled to and/or communicate with a mobile electronic device and to systems and methods for acquiring, logging, and/or maintaining temperature records for food products using such an apparatus.

In accordance with an exemplary embodiment, a system is provided for logging temperatures of food products that includes a temperature assembly including a housing and a temperature probe, e.g., an infrared probe, for acquiring a temperature of a food product; and a mobile electronic device including a camera, a communication interface for communicating with the temperature assembly, a processor configured to acquire a temperature reading from the temperature assembly and an image from the camera when the temperature reading is acquired, and memory for storing the temperature reading and image.

In accordance with another exemplary embodiment, a system is provided for logging temperatures of food products at a physical location that includes a mobile electronic device including a camera; a temperature assembly including a housing configured to removably secure the temperature assembly to the mobile electronic device, and an infrared sensor for acquiring a temperature of a food product in a predetermined direction aligned with a field of view of the camera; the mobile electronic device and temperature assembly including one or more communication interfaces for communicating with one another; the mobile electronic device comprising a processor configured to acquire a temperature reading from the temperature sensor and an image from the camera when a temperature reading is acquired, and memory for storing the temperature reading and image.

In accordance with yet another embodiment, a method is provided for acquiring temperature data of food products that includes providing a mobile electronic device and a temperature assembly including a temperature probe coupled to the mobile electronic device; selecting a food product from a menu on a display of the mobile electronic device; and activating the mobile electronic device to acquire a temperature of the selected food product using the temperature probe and substantially simultaneously acquire an image using a camera of the mobile electronic device of the food product.

In accordance with another embodiment, a method is provided for acquiring temperature data of food products that includes providing a mobile electronic device and a temperature assembly including a temperature probe coupled to the mobile electronic device; directing the temperature probe towards a container including a food product, whereupon the food product is automatically identified on a display of the mobile electronic device; and activating the mobile electronic device to acquire a temperature of the identified food product using the temperature probe and substantially simultaneously acquire an image using a camera of the mobile electronic device of the food product. For example, a processor of the mobile electronic device or the apparatus may use object recognition to automatically identify the food product based on the image acquired using the camera and prompt the user to confirm that the correct food product has been identified.

In accordance with still another embodiment, a method is provided for acquiring temperature data of a remote object that includes mounting a temperature assembly to a mobile electronic device such that an infrared sensor of the temperature assembly is aligned with a field of view of a camera of the mobile electronic device; orienting the infrared sensor towards a target object; and acquiring a temperature of the object with the infrared sensor and an image of the object with the camera.

In accordance with another embodiment, a method is provided for acquiring temperature data of food products that includes mounting a temperature assembly to a mobile electronic device such that an infrared sensor of the temperature assembly is aligned with a field of view of a camera of the mobile electronic device; orienting the infrared sensor towards a container including a food product; and acquiring a temperature of the food product with the infrared sensor and an image of the food product with the camera. Optionally, the food product may be automatically identified and an identifier presented on the display, e.g., along with an image of the food product acquired from the camera and/or along with a dot or other pointer indicating the direction in which the infrared sensor is oriented, e.g., such that the user may confirm that the infrared sensor is oriented towards a desired container and/or food product.

In accordance with yet another embodiment, a method is provided for acquiring temperature data of food products that includes mounting a temperature assembly to a mobile electronic device such that a tip of a temperature probe extending from the temperature assembly is within a field of view of a camera of the mobile electronic device; inserting the tip of the temperature probe into a food product in a container; and acquiring a temperature of the food product with the temperature probe and an image of the food product with the camera.

Other aspects and features including the need for and use of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments, in which.

DESCRIPTION OF THE EXEMPLARY EMBODIMENTS

Turning to the drawings, FIGS. 1A-2B show an exemplary embodiment of a system 8 for logging temperature information for food products, e.g., to facilitate a restaurant or other food services business acquiring, logging, and/or maintaining desired temperature records for ingredients or other food products stored and/or used at the business.

Figures 1A, 1B, 3A, 3B:
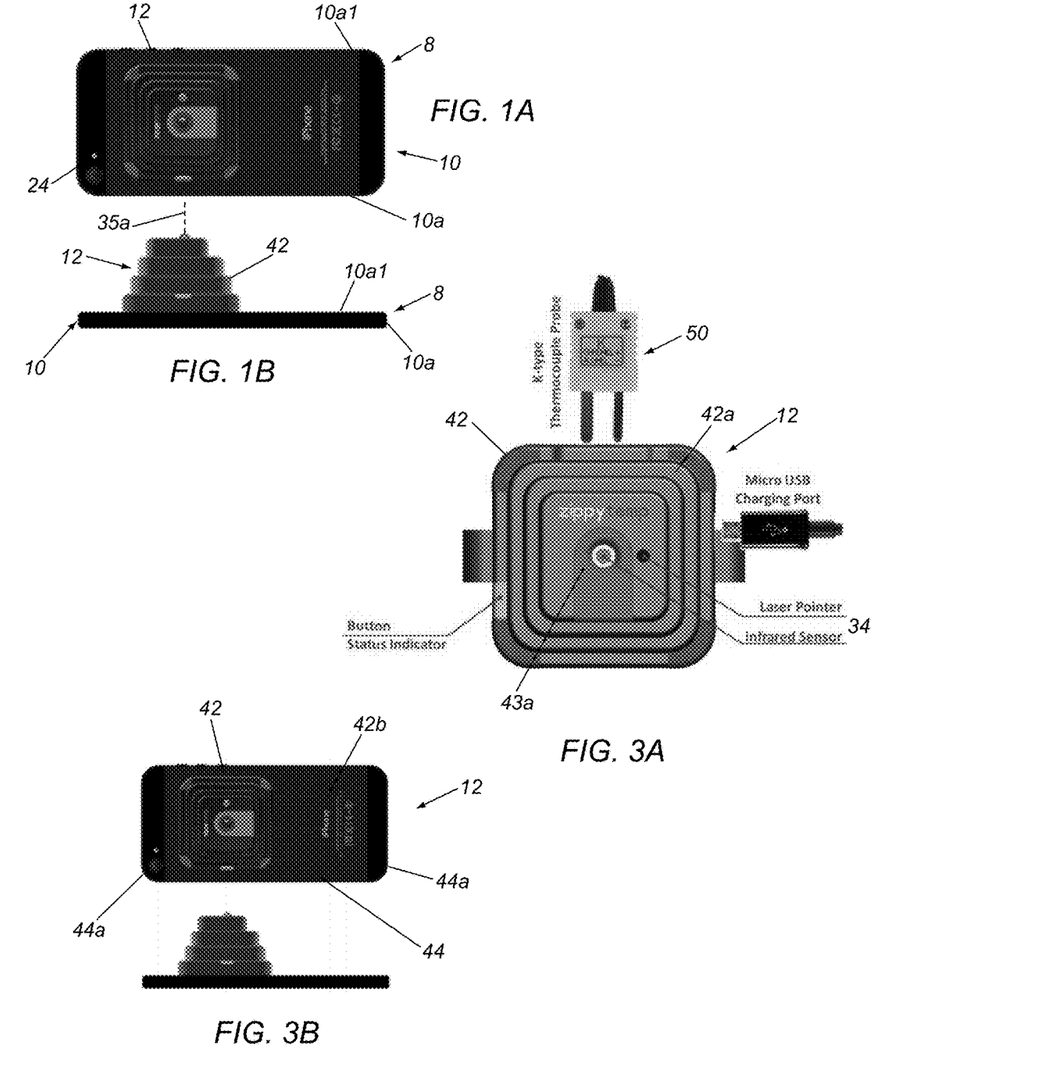
FIGS. 1A and 1B are top and side views, respectively, of an exemplary embodiment of a system including a temperature sensing apparatus coupled to a mobile electronic device.
FIG. 3A is a front view of the temperature sensing apparatus of FIGS. 1A and 1B, showing features of the apparatus.
FIG. 3B is a rear view of the temperature sensing apparatus of FIGS. 1A and 1B, showing a bracket for releasably securing the apparatus to a mobile electronic device.
Figure 4:
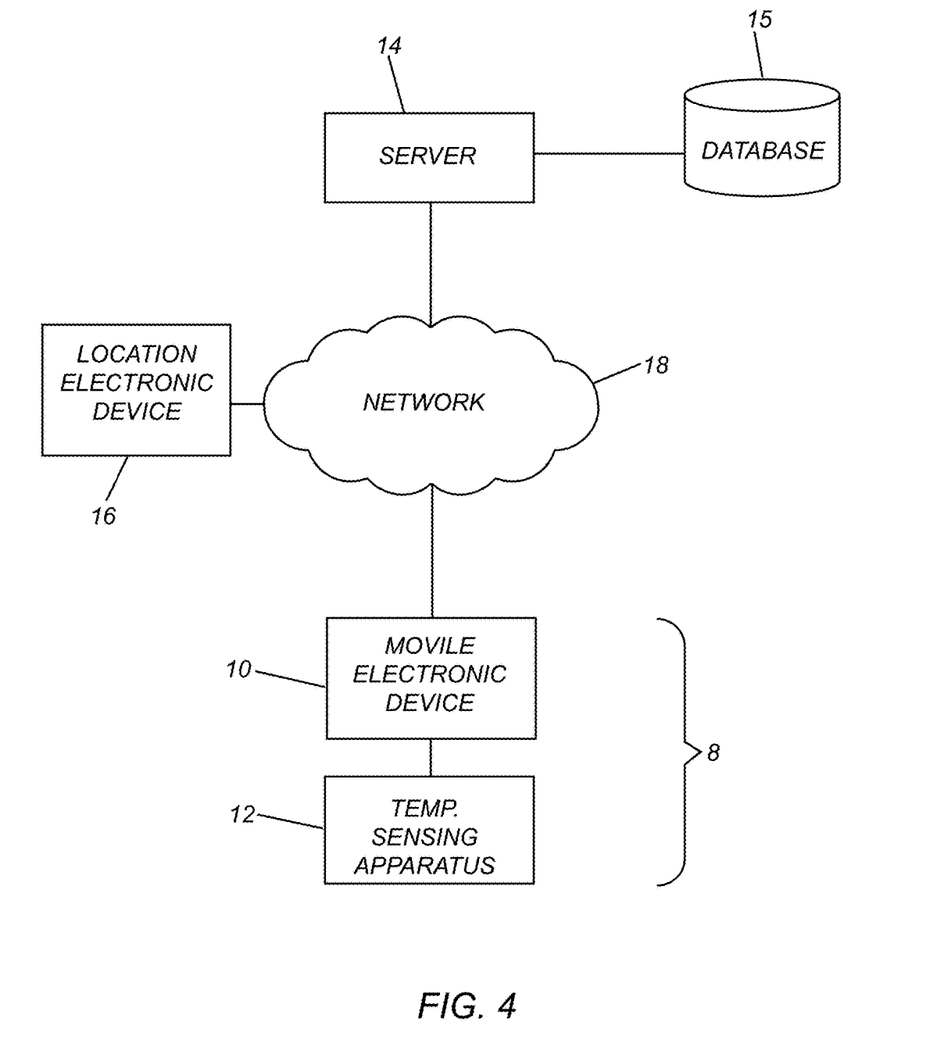
FIG. 4 is a schematic drawing showing an exemplary network architecture within which a system such as that shown in FIGS. 1A and 1B may communicate with other electronic devices to log and/or maintain temperature records.

Generally, as shown in FIGS. 1A and 1B, the system 8 includes a mobile electronic device 10 and a temperature assembly or sensing apparatus 12, which may be coupled to and/or communicate with the electronic device 10 to perform the various functions described herein. Optionally, as shown in FIG. 4, the system 8 may communicate with one or more additional electronic devices, e.g., a remote administrative server 14 and/or a location electronic device 16, e.g., a cash register or other point-of-sale device at the same location as the electronic device 10, via a network 18, as described further elsewhere herein. Optionally, multiple systems 8 may be provided at a single location and/or multiple locations (not shown), which may communicate with the server 14 and/or other devices via the network 18, e.g., to allow multiple systems 8 to acquire temperature information simultaneously and/or to allow multiple locations to store and/or access temperature information in a database 15 maintained by the server 14, e.g., as described elsewhere herein.

The mobile electronic device 10 may be a portable or mobile device, which may be carried by an employee or other user throughout a restaurant or other location to acquire temperature information for desired food products, as described elsewhere herein. In an exemplary embodiment, the mobile electronic device 10 may be a smart mobile device, e.g., an iPhone®, Android®, or other smart phone device, an iPad® or other tablet device, and the like, running a software application performing the various functions and features described herein.

Figure 2A:
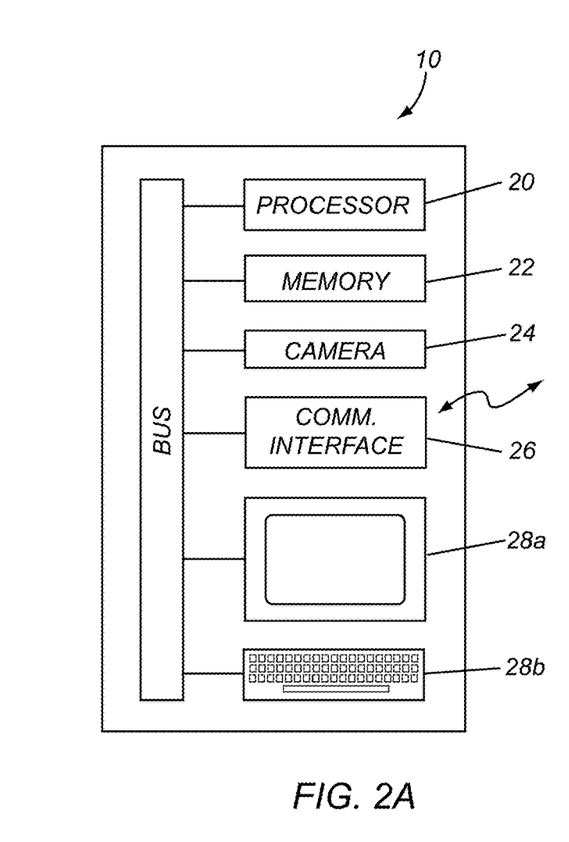
FIGS. 2A and 2B are schematics of exemplary embodiments of a temperature sensing apparatus and a mobile electronic device, respectively.

As shown in FIG. 2A, the mobile electronic device 10 generally includes one or more processors (one processor 20 shown), memory 22, a camera 24, a communication interface 26, and one or more user interfaces 28, e.g., a display or other output device 28a, and a touch screen, keyboard, mouse, touch pad, and/or other input device 28b. The input device(s) 28b may facilitate a user controlling and/or otherwise communicating with the processor 22 or other components of the electronic device 10 and/or the temperature sensing apparatus 12, while the output device(s) 28a may allow information to be presented and/or manipulated in a desired manner, e.g., to present a series of menus, fields, pages, and/or other images, as described elsewhere herein. In one embodiment, the electronic device 10 may include a touch screen (not shown) that may act as a display 28a and as an input device 28b, allowing the user to scroll through menus or images, and/or select icons, e.g., by touching or otherwise selecting corresponding images on the touch screen, as described elsewhere herein.

In an exemplary embodiment, the communication interface 26 includes one or more transceivers, receivers, and/or transmitters, e.g., a short range transceiver for communicating with the temperature sensing apparatus 12 and/or a long range transceiver, e.g., to communicate with the server 14 and/or location electronic device 16 via the network 18. In an exemplary embodiment, the short range transceiver may communicate wirelessly using radiofrequency signals, such as Bluetooth or other protocols. Alternatively, a wired communication interface (not shown) may be provided for communicating with the temperature sensing apparatus 12, if desired. For example, in this alternative, the electronic device 10 and/or temperature sensing apparatus 12 may include one or more connectors and a cable may be coupled between them via the connector(s) (not shown).

The long range communication interface may allow software and/or data to be transferred between the electronic device 10 and the server 14, the location electronic device 16, and/or other external devices, networks, or information sources. For example, the long range communication interface may communicate via existing networks, e.g., telecommunications networks, the Internet, and the like, as represented by the network 18 shown in FIG. 4. Alternatively, the short range transceiver may be used to communicate with one or more remote devices, the location electronic device 16, and the like via a local wireless network.

Figure 2B:
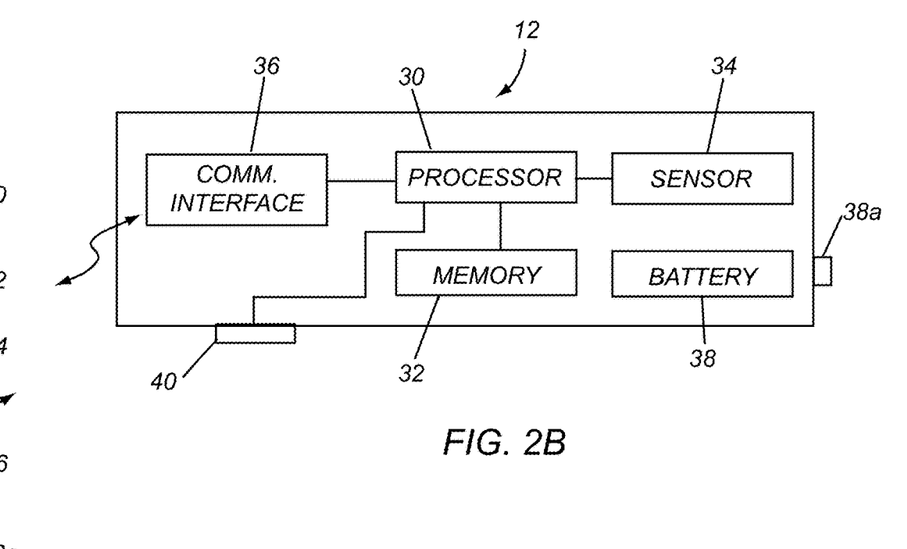

Turning to FIG. 2B, the temperature sensing apparatus 12 generally includes one or more processors (e.g., one processor 30 shown), memory 32, a temperature sensor 34, and a communication interface 38. In an exemplary embodiment, the communication interface 38 may be a short range transceiver that communications with the mobile electronic device 10 via the communication interface 26, e.g., using radiofrequency signals, such as Bluetooth or other protocols.

Optionally, the temperature sensing apparatus 12 may include one or more additional components, e.g., a battery or other power source 38, and/or a probe connector 40, e.g., for coupling a thermocouple or other probe 50 to the apparatus 12, e.g., as shown in FIG. 3A. For example, a k-type thermocouple probe 50 may be coupled to the apparatus 12 that includes a tip (not shown) that may be inserted into a food product to acquire the temperature of the product.

Figure 5A:
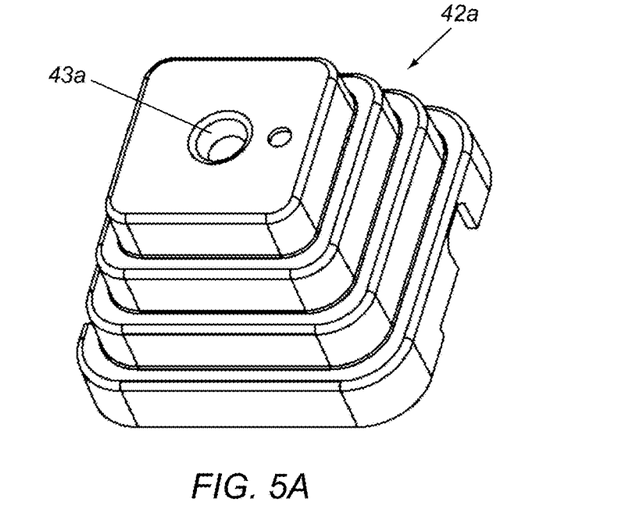
FIGS. 5A-5D show perspective, top, side, and bottom views, respectively, of an exemplary embodiment of a front housing for the apparatus of FIGS. 3A and 3B.
Figure 5B:
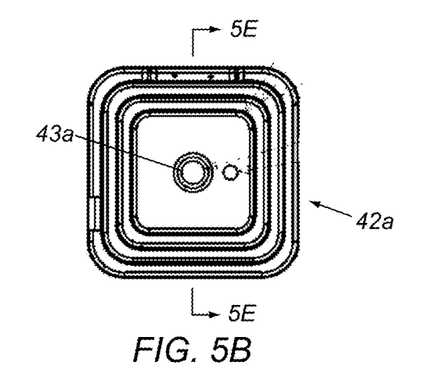
Figure 5C:
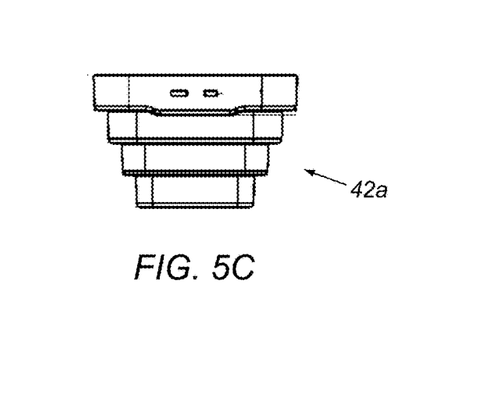
Figure 5D:
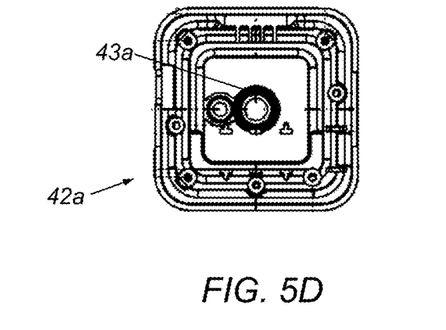
Figure 5E:
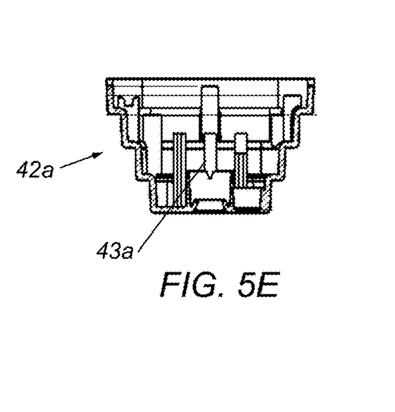
FIG. 5E is a cross-sectional view of the front housing of FIGS. 5A-5D taken along line 5E-5E of FIG. 5B.
Figure 6A:
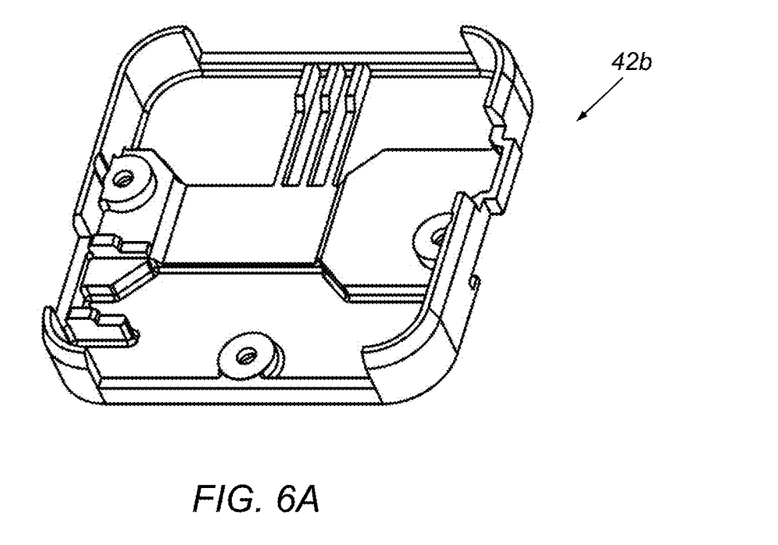
FIGS. 6A-6C show perspective, front, and side views, respectively, of an exemplary embodiment of a back housing for the apparatus of FIGS. 3A and 3B.
Figure 6B:
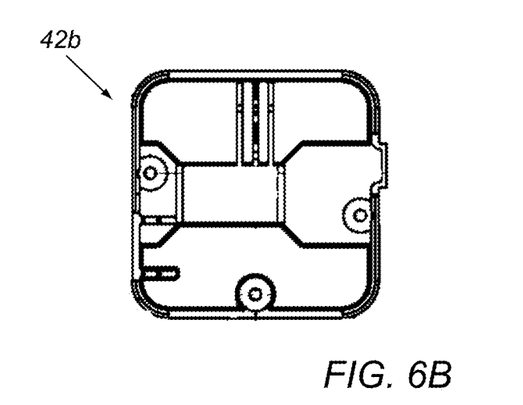
Figure 6C:
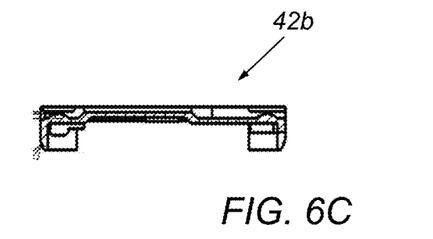
Figure 7A:
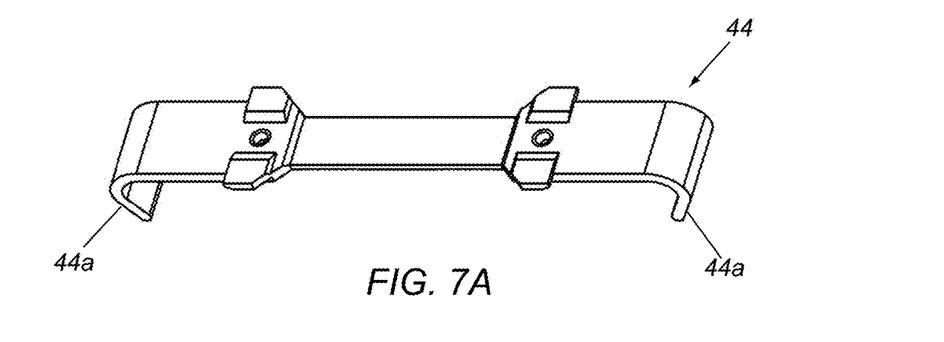
FIGS. 7A-7C show perspective, front, and bottom views, respectively, of an exemplary embodiment of a bracket that may be provided on the apparatus of FIGS. 3A and 3B that include fingers or other elements for coupling the apparatus to a mobile electronic device.
Figure 7B:
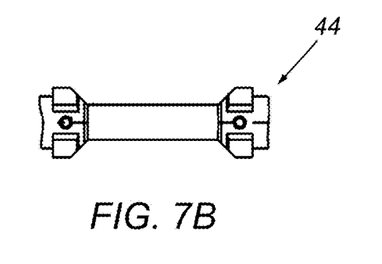
Figure 7C:
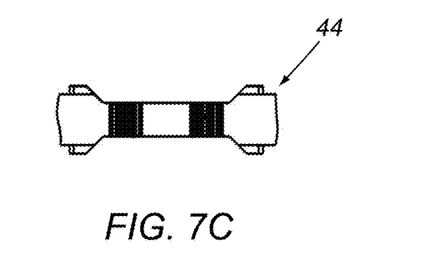
Figure 7D:
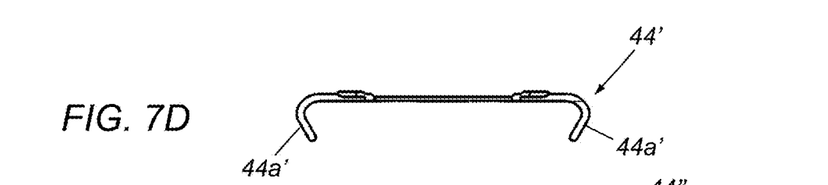
FIGS. 7D-7F show alternative brackets having different finger spacings to accommodate mounting the bracket to different size mobile electronic devices.
Figure 7E:
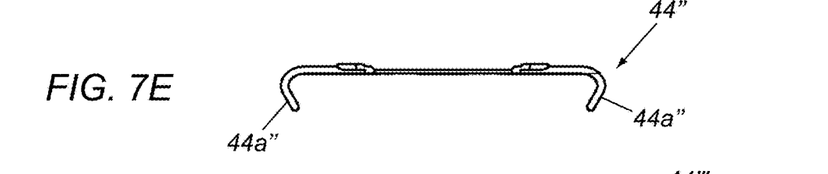
Figure 7F:
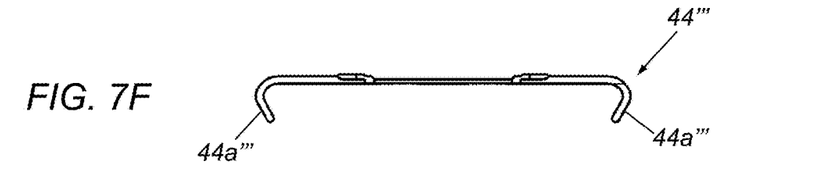

With additional reference to FIGS. 3A and 3B, the components of the apparatus 12 may be contained within a housing 42, e.g., including a top housing 42a (e.g., as shown in FIGS. 5A-5E) and a back housing or base 42b (e.g., as shown in FIGS. 6A-6C), which may be connected together to substantially seal and/or otherwise protect the components therein. In addition, the housing 42 may include one or more connectors for releasably coupling the apparatus 12 to the mobile electronic device 10. For example, as shown in FIG. 3B, a bracket 44 (e.g., as shown in FIGS. 7A-7C) may be provided on the back housing 42b that includes one or more features, e.g., fingers 44a that may engage the casing of the mobile electronic device 10. Optionally, as shown in FIGS. 7D-7F, a plurality of brackets 44,' 44," 44'" may be provided that have different shapes and/or configurations that may be selectively coupled to the housing 42 to allow the apparatus 12 to be mounted to different mobile electronic devices. For example, a set of brackets may be provided that include fingers 44a having different spacings, and the user may secure the appropriate bracket to the housing 42 that corresponds to the mobile electronic device being used. Alternatively, a single bracket may be provided that is adjustable (not shown) such that the spacing of the fingers 44A may be changed to allow the bracket 44 to be selectively locked to accommodate attachment to different size mobile electronic devices. For example, the bracket may include two sections that are slidable relative to one another (not shown), e.g., to adjust the spacing of the fingers 44a to different distances, e.g., as shown in FIGS. 7D-7F. In this alternative, the sections may include cooperating ratchets, detents, and the like (not shown) that may fix the fingers 44a at predetermined distances. In a further alternative, multiple apparatus 12 may be provided with different brackets substantially permanently secured thereto for mounting each apparatus 12 to a mobile electronic device having a corresponding shape.

Before use, the apparatus 12 may be mounted to a casing 10a of the mobile electronic device 10, e.g., by positioning the back housing 42b of the apparatus 12 against a corresponding surface of the casing 10a, e.g., a back surface 10a1 of the electronic device 10 (e.g., opposite the touch screen and/or other user interface of the electronic device 10, not shown). For example, a user may position the back 42a of the housing 42 adjacent the back surface 10a1 of the casing 10a adjacent the camera 24 such that the bracket 44 extends across the casing 10a and the apparatus 12 may be pressed against the casing 10a until the fingers 44a of the bracket 44 snap around the casing 10a, thereby securing the apparatus 12 to the electronic device 10, as shown in FIGS. 1A and 1B. The fingers 44a may provide an interference fit with the casing 10a to prevent substantial movement of the apparatus 12 relative to the electronic device 10. Yet, at any time, the user may pull the apparatus 12 away from the electronic device 10, thereby overcoming the interference fit and causing the fingers 44a to resiliently expand and release the apparatus 12 from the electronic device 10. In an alternative embodiment, the bracket 44 may be adjustable, e.g., to change the spacing of the fingers 44a to different distances, e.g., as shown in FIGS. 7D-7F. In another alternative embodiment, a specialized mobile electronic device may be provided that includes the components of the temperature sensing apparatus integrally provided in the electronic device (not shown).

When the apparatus 12 is properly secured to the electronic device 10, the camera 24 may be exposed adjacent the apparatus 12, as shown in FIG. 1A. For example, the camera 24 may have a field of view that includes the line of sight of the sensor 34 or probe of the apparatus 12, e.g., such that a photograph may be taken of a food product when a temperature of that food product is taken, as described further below.

As best seen in FIGS. 3A and 5E, in an exemplary embodiment, the temperature sensor 34 of the apparatus 12 includes an infrared sensor 34a mounted within the housing 42 such that the sensor 34a is positioned within or oriented towards an opening 43a in the front housing 42, e.g., such that the sensor 34a is configured to acquire temperature data along the line of sight corresponding to sensor axis 35a, as shown in FIG. 1B. In addition, the temperature sensor 34 may include a guide 34b, e.g., a laser pointer 34b, mounted in the housing 42 such that the guide 34b directs a beam of light substantially parallel to or converging on the sensor axis 35a. Consequently, during use, the guide 34b may direct a dot or other image in a direction towards which the infrared sensor 34a is pointed, e.g., to indicate to the user when a food product is within the line of sight of the infrared sensor 34a as well as the camera 24 of the mobile electronic device 10.

Similarly, if a thermocouple or other probe 50 is coupled to the apparatus 12, the probe 50 may have a substantially fixed shape such that a tip of the probe lies within the field of the view of the camera 24. The beam of light from the guide 34b may provide a dot or other image on a food product or surface towards which the tip of the probe is oriented and/or into which the tip is inserted.

At any time before use, a software application may be installed in the mobile electronic device 10, e.g., in memory 22, that allows the device 10 to communicate with the temperature sensing apparatus 12, e.g., to acquire temperature information and/or communicate such information with a remote device, such as the server 14 and/or location electronic device 16. The application may also include a series of menus to facilitate the user acquiring temperature of particular food products and/or locations, e.g., which may be navigated using the user interface 26.

For example, the software application may be initially downloaded into memory 22 via the communication interface 26, e.g., from the server 14 and/or an independent application vendor's server. In addition, the application may be automatically upgraded at desired intervals, e.g., each time the apparatus 12 is coupled to the mobile electronic device 10, when the application is initially launched, when the network 18 is detected, and/or at periodic internals. During any such upgrades, firmware or software in the apparatus 12 itself may be upgraded, if desired, in addition to the application stored in the memory 22 of the mobile electronic device 10.

One the application is installed and/or updated, the application may be used to acquire temperature data using the apparatus 12. For example, a particular restaurant or business may have a preset list of food products for which temperature data should be acquired, e.g., multiple times per day or at other periodic or regular intervals. In an exemplary embodiment, a Subway® restaurant may include a food preparation area including a plurality of food containers storing particular ingredients for making sandwiches, salads, or other food products. Such ingredients may include meats, cheese, vegetables, and the like, placed in individual containers, which are to be maintained at particular refrigerated temperatures. In addition, some meats or other ingredients, soups, and the like may be placed in individual containers, which are to be maintained at particular heated temperatures. The system 8 may be used to acquire temperature readings for each of these containers, e.g., to create a log of temperatures for the restaurant.

For example, the application may include a menu of such food products, e.g., organized by refrigerated food products and heated food products and/or separated based on different areas within the restaurant. The application may prompt the user when temperature data are scheduled to be acquired, e.g., by providing reminders or other scheduling information on the display 28a of the mobile electronic device 10. In addition or alternatively, a location electronic device 16, e.g., a point-of-sale device at the restaurant, may provide reminders that temperature data is due, e.g., by presenting a pop-up image on a display of the location electronic device 16, which may remain on the display until the scheduled data is acquired and logged. Optionally, the reminder may lock-out the location electronic device 16, e.g., prevent further sales and/or other activities, until the scheduled temperature data is acquired.

Once reminded, the user may obtain the system 8, e.g., by mounting the apparatus 12 to their personal mobile device including the application, by mounting the apparatus 12 to a location-specific mobile device 10, or by simply obtaining the apparatus 12 already mounted to (or integrated into) a mobile device at the restaurant. Optionally, once the apparatus 12 is mounted to the mobile electronic device 10 or otherwise activated, any reminder on the location electronic device 16 may be removed (e.g., instead of locking-out the location electronic device 16).

The user may then activate the apparatus 12, e.g., by turning on the apparatus 12 via a switch or other actuator (not shown), and/or via the menu or interface on the display 28a of the mobile electronic device 10 to obtain the scheduled temperatures. Once activated, a menu may be presented on the display 28a from which the user may select the food products and acquire temperatures of the selected food products stored within respective containers at the restaurant. Alternatively, the food products may be presented in a preset order such that the user sequentially acquires the temperatures of the food products by navigating through the menu.

When an individual temperature is to be acquired, with the appropriate food product identified on the menu, the sensor 34 and camera 24 may be oriented towards the food product and/or its container. Optionally, the apparatus 12 may be activated from a dormant state, e.g., by selecting a button on the apparatus 12 or on the menu on the display 28a. Optionally, an indicator light may be provided on the apparatus 12, e.g., to confirm when the apparatus 12 is ready to be used. The user may then activate the apparatus 12 to acquire the temperature. In addition and/or optionally, the system 8 may acquire an image of the food product and/or container with the field of view of the camera 24 to confirm that the food product matches the menu selection presented on the display 28a before allowing temperature acquisition, as explained below. Once the food product has been confirmed, the system 8 may allow the user to proceed to acquiring the temperature.

When the apparatus 12 is activated, the temperature sensor 34a may acquire a temperature of the food product within the line of sight of the sensor 34, e.g., using the infrared sensor 34a. Substantially simultaneously, the camera 24 may acquire an image of the food product towards which the sensor 34 is oriented. The processor 20 of the mobile electronic device 10 may save the temperature and image together in memory 22, thereby providing a record of the food product associated with the acquired temperature. Optionally, the processor 20 may associate a time stamp, food product identifier, and/or other information with the temperature/image record, e.g., to provide additional information regarding a particular temperature reading.

Figure 8A:
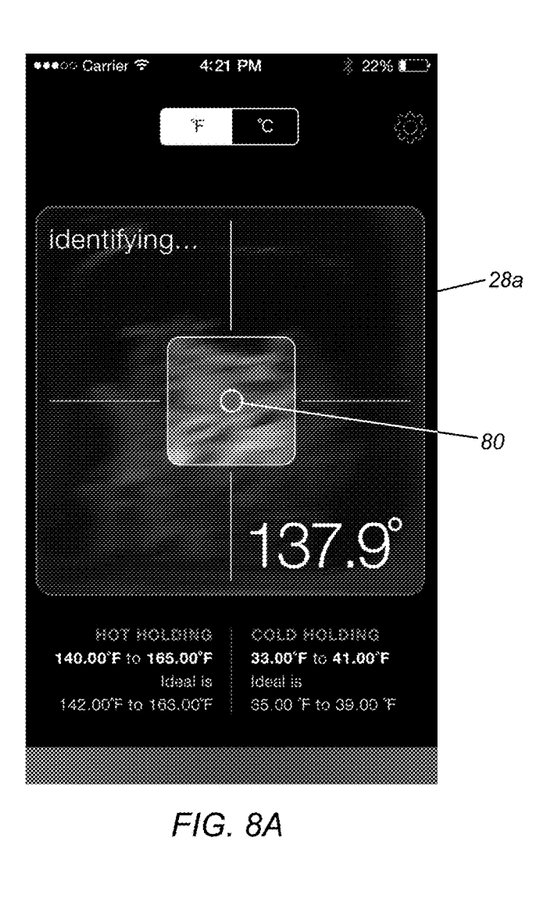
FIGS. 8A-8E show exemplary images of food products and temperature readings that may be acquired using the apparatus and methods herein.
Figure 8B:
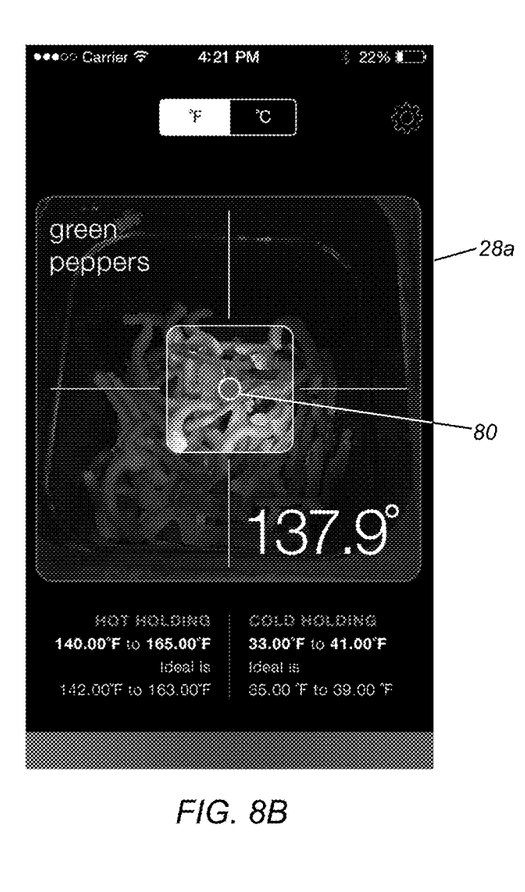

Optionally, the processor 20 may automatically identify a food product within the field of view of the camera 24 before temperature acquisition, e.g., using a database of images, object recognition, and/or other algorithms. For example, as shown in FIGS. 8A and 8B, when the user points the camera 24 towards a container of food products, e.g., green peppers, the processor 20 may identify the food product (green peppers) in the camera images, e.g., indicate that the food product is being identified, as shown in FIG. 8A, and automatically prompt the user that this is the intended food product, as shown in FIG. 8B. In addition, as shown, acceptable temperature ranges may be presented on the display 28a, e.g., based on types of food product. For example, the acceptable temperature ranges may include a range for hot food products, e.g., meat balls, or cold good products, e.g., green peppers, as shown in FIGS. 8A and 8B.

Once the user confirms the food product, the processor 20 may automatically acquire the temperature using the sensor 34 or upon activation by the user. Optionally, a real-time temperature reading may be presented on the display, e.g., as shown in FIGS. 8A-8E. Thus, this option may ensure that the temperature data is acquired for the correct food product, which may reduce user error.

In addition or alternatively, real-time images of the food product and/or its container may be presented on the display 28a of the mobile electronic device 10, e.g., to facilitate the user accurately orienting the sensor 34 towards the food product. For example, as shown in FIGS. 8A-8E, the processor 20 may superimpose a graphic 80, e.g., a dot, circle, or other character on the images, e.g., surrounding the dot from the guide 34b, to assist the user. Optionally, the processor 20 may analyze the images, e.g., to ensure that the sensor 34 is oriented properly to reduce the risk of inaccurate temperature readings. For example, if the sensor 34 is oriented towards the wall of a stainless steel container rather than into the food products in the container, temperature readings may be inaccurate due to light being reflected by the stainless steel wall. The processor 20 may prompt the user on the display 28a when this occurs, e.g., to suggest the user orient the sensor 34 away from the wall and into the center of the container, thereby enhancing the accuracy of the resulting temperature reading.

Optionally, the processor 20 may analyze the camera images to ensure that the user positions the sensor 34 at a desired distance from the container. For example, the processor 20 may provide visual confirmation on the display 28a when the sensor 34 is positioned within an acceptable range of distances from the container, e.g., since the sensor 34 may have optimal distances for acquiring accurate temperatures.

In addition or alternatively, a probe 50 may be coupled to the apparatus 12 and inserted into a food product to acquire a temperature of the food product. For example, the infrared sensor 34a may be used to acquire temperatures of refrigerated food products, while the probe 50 may be used to acquire temperatures of heated food products (since the infrared sensor 34a may not accurately acquire temperatures of heated food products given that the surface temperature may not accurately reflect the overall temperature of heated food products). Optionally, the probe 50 may be cleaned such that the probe 50 may be inserted sequentially into different food products to acquire multiple temperature readings. Alternatively, a disposable sleeve (not shown) may be positioned over the probe 50, which may be removed after each temperature reading to allow the probe 50 to be used for multiple food products. In a further alternative, the probe 50 may be removed after each temperature reading and a new probe coupled to the apparatus 12 for each additional temperature reading.

Once a series of temperatures is acquired, e.g., upon acquiring temperatures of all scheduled food products on the menu presented on the display 28a of the mobile electronic device 10, the processor 20 may transfer the data to a remote device, e.g., to the server 14 for storage in the database 15 and/or to the location electronic device 16. Alternatively, after each temperature/image is acquired, the processor 20 may transfer the data to the server 14 and/or location electronic device 16, thereby sending individual batches as each food product is selected from the menu.

Optionally, when one or more temperatures are acquired, the application may present one or more remedial actions or reminders to the user, e.g., on the display 28a of the mobile electronic device 10 and/or on a display of the location electronic device 16. For example, if the temperature of a refrigerated meat product is acquired, but is outside an accepted range, e.g., too warm, the user may be prompted immediately and suggested to act, e.g., turn down the thermostat on a refrigeration system associated with the container, check fluid or ice levels, and the like, as appropriate for the configuration of the location where the container is stored. Thus, this option may facilitate taking immediate action to troubleshoot potential problems before food products become spoiled or otherwise at risk.

Figure 8C:
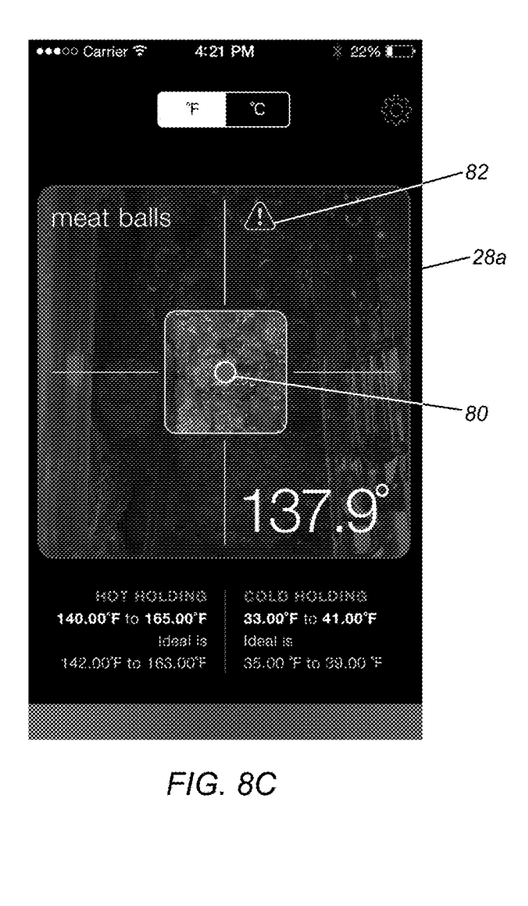
Figure 8D:
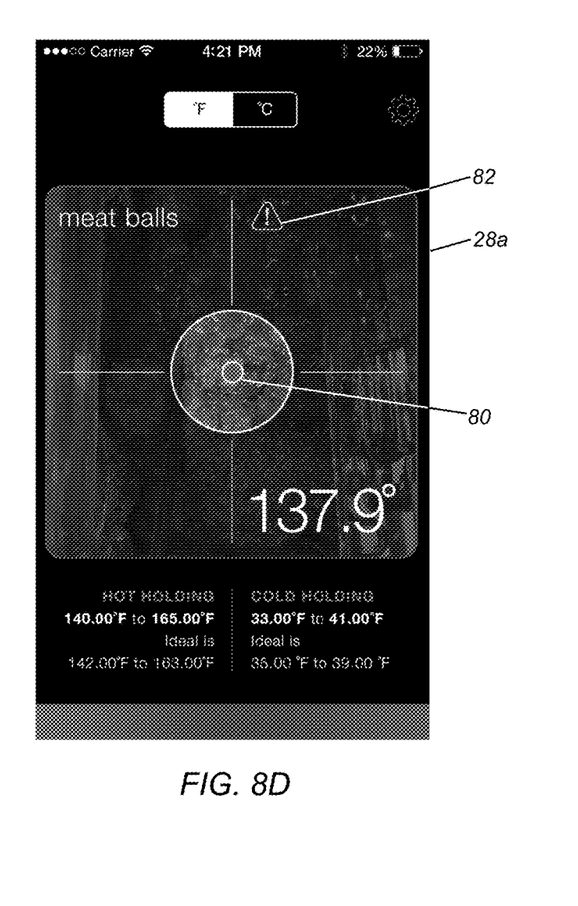
Figure 8E:
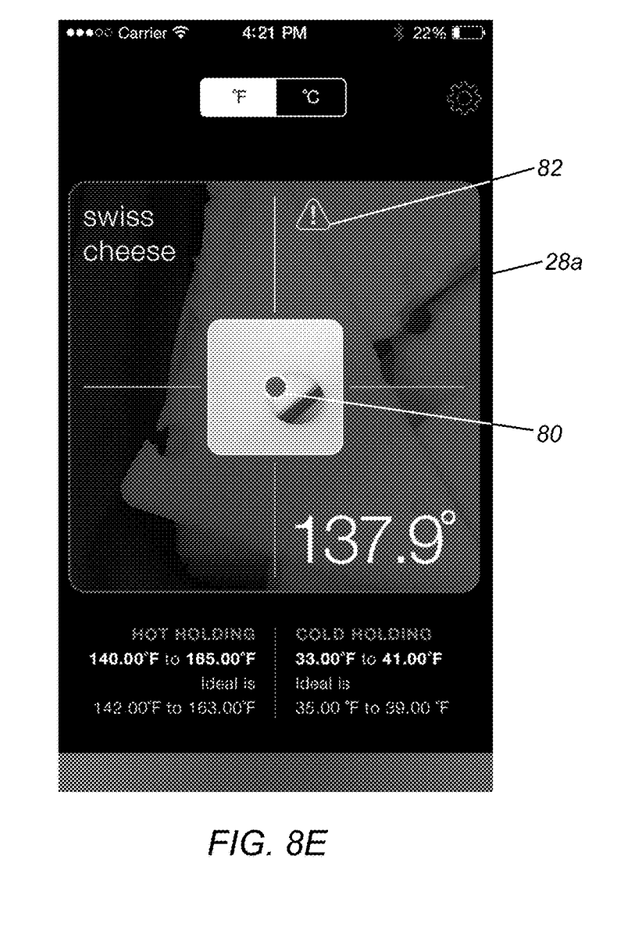

For example, FIGS. 8C-8E show a warning icon (yellow triangle 82) indicating that the acquired temperature may be outside the desired range for the identified food product. Optionally, as shown, the desired range or ranges for the identified food product may be presented on the display 28a, e.g., adjacent real-time images and/or temperature readings, as shown.

At any time, a report may be generated of the temperatures acquired using the system 8. For example, a user at the restaurant or other location where the temperatures were acquired may use the location electronic device 16 to generate a report of the temperatures, e.g., presenting the data on a display and/or printing a hard copy of the temperatures/images/time stamps, e.g., for a particular session, day, and/or other interval. Similarly, a manager, inspector, or other authorized person may access the data via the server 14 to generate desired reports from the location electronic device 16 or other remote device.

Thus, using the system 8, temperature records may be maintained to ensure that the acquired temperatures are properly taken for the associated food products. The image provides visual confirmation that the acquired temperature was taken for the actual food product identified from the menu. Thus, if a user acquired a temperature for an incorrect food product, a manager may identify the error easily since the image will not match the food product identified from the record. Such errors can then be remedied, e.g., by improving training of users or investigating intentional fraud.

In addition, the temperature sensing apparatus 12 may allow any compatible mobile electronic device to be used to acquire temperature data. For example, when not in use, the temperature sensing apparatus 12 may be stored at a desired location within the restaurant or other business, e.g., plugged in such that the power source 38 may be recharged. A user may unplug or otherwise prepare the apparatus 12, mount it to their mobile electronic device 10 (or alternatively to a dedicated mobile electronic device at the business), and then use the resulting system 8 to acquire temperature data, as described elsewhere herein.

Although the exemplary embodiments described above relate to systems and methods for acquiring temperature data for food products, it will be appreciated that a modular temperature sensing apparatus and associated software application may be used with mobile electronic devices to acquire temperatures for other objects as well, e.g., surfaces of food preparation areas, surfaces or equipment within manufacturing facilities, and the like, where it may be desirable to acquire real-time temperature readings. Thus, the systems and methods herein may allow users to acquire real-time temperatures and images of objects simply using a conventional smart mobile device. The resulting data may be stored locally, transmitted to a remote server or other location, and/or analyzed, as desired.

While the invention is susceptible to various modifications, and alternative forms, specific examples thereof have been shown in the drawings and are herein described in detail. It should be understood that the invention is not to be limited to the particular forms or methods disclosed, but to the contrary, the invention is to cover all modifications, equivalents and alternatives falling within the scope of the appended claims.

I claim:

1. A system for logging temperatures of food products, comprising:

a temperature assembly including a housing and a temperature probe for acquiring a temperature of a food product; and a mobile electronic device including a camera, a communication interface for communicating with the temperature assembly, a processor configured to acquire a temperature reading from the temperature assembly and an image from the camera when the temperature reading is acquired, and memory for storing the temperature reading and image, wherein the temperature assembly comprises a connector for releasably securing the temperature assembly to the mobile electronic device such that the temperature probe is fixed relative to the mobile electronic device and acquires temperature readings in a direction aligned with a field of view of the camera.

2. The system of claim 1, wherein the temperature probe comprises an elongate probe including a tip configured for insertion into a food product.

3. The system of claim 2, wherein the temperature probe is removably coupled to the housing such that the elongate probe has a substantially fixed shape such that the tip lies within the field of the view of the camera.

4. The system of claim 1, wherein the connector comprises a bracket coupled to the housing, the bracket including a plurality of elements for engaging a case of the mobile electronic device.

5. The system of claim 1, wherein the temperature probe comprises an infrared sensor having a line of sight for remotely acquiring temperatures in a direction aligned with the field of view of the camera.

6. The system of claim 1, wherein the mobile electronic device comprises a display, and wherein the processor is configured for presenting a menu on the display including one or more food products for which temperature readings are scheduled, the mobile electronic device comprising a user interface for selecting a food product from the menu and activating the processor to acquire a temperature reading and image of the selected food product.

7. The system of claim 1, wherein the processor is configured for storing the temperature reading and image along with a time stamp indicating when the temperature reading and image were acquired.

8. The system of claim 1, wherein the temperature assembly comprises a wireless transmitter for sending temperature readings to the communication interface of the mobile electronic device.

9. The system of claim 1, wherein the communication interface comprises a cable for communicating between the mobile electronic device and the temperature assembly.

10. The system of claim 1, further comprising a location electronic device communicating with the mobile electronic device via a network, the location electronic device configured to generate a report including temperature readings and images acquired using the mobile electronic device and the temperature assembly.

11. The system of claim 1, wherein the camera is provided on a back surface of the mobile electronic device opposite a display of the mobile electronic device, and the temperature assembly is mounted to the back surface of the mobile electronic device such the temperature probe is aligned with the field of view of the camera.

12. The system of claim 1, wherein the processor is configured to:

automatically, based on one or more images from the camera, identify a food product within the field of view of the camera before temperature acquisition; and prompt the user that the identified food is the food product intended for temperature acquisition.

13. A system for logging temperatures of food products at a physical location, comprising:

a mobile electronic device including a camera;

a temperature assembly including a housing configured to removably secure the temperature assembly to the mobile electronic device, and an elongate temperature probe coupled to the housing and having a substantially fixed shape such that the tip lies within the field of the view of the camera when the housing is secured to the mobile electronic device;

the mobile electronic device and temperature assembly including one or more communication interfaces for communicating with one another;

the mobile electronic device comprising a processor configured to acquire a temperature reading from the temperature probe and an image from the camera when a temperature reading is acquired, and memory for storing the temperature reading and image.

14. The system of claim 13, wherein the mobile electronic device comprises a display, and wherein the processor is configured for presenting a menu on the display including one or more food products for which temperature readings are scheduled, the mobile electronic device comprising a user interface for selecting a food product from the menu and activating the processor to acquire a temperature reading and image of the selected food product.

15. The system of claim 13, wherein the processor is configured for storing the temperature reading and image along with a time stamp indicating when the temperature reading and image were acquired.

16. The system of claim 13, wherein the one or more communication interfaces comprise wireless transceivers in the mobile electronic device and the temperature assembly.

17. The system of claim 13, further comprising a location electronic device at the physical location, the location electronic device comprising a location processor and a location display, the location processor configured to present a reminder on the location display when one or more temperature readings are due.

18. The system of claim 17, wherein the location processor is configured to lock-out the location electronic device once a reminder is presented until the one or more temperature readings that are due are acquired.

19. The system of claim 17, wherein the location processor is configured to remove the reminder from the location display when the temperature assembly is activated to acquire the one or more temperature readings that are due.

20. The system of claim 13, wherein the processor is configured to identify a food product in an image from the camera, present a label on the display, and request confirmation from the user before a temperature reading of the identified food product is acquired.

21. A method for acquiring temperature data of food products by a user, comprising:

providing a mobile electronic device including a camera, and a temperature assembly including an elongate temperature probe coupled to the mobile electronic device, the probe having a substantially fixed shape such that a tip of the probe lies within a field of the view of the camera;

selecting a food product from a menu on a display of the mobile electronic device;

inserting the tip into a food product; and activating the mobile electronic device to acquire a temperature of the selected food product using the temperature probe and substantially simultaneously acquire an image using a camera of the mobile electronic device of the food product.

22. The method of claim 21, further comprising storing the acquired temperature and image in memory of the mobile electronic device, along with a time stamp identifying when the temperature and image were acquired.

23. The method of claim 22, further comprising communicating the acquired temperature and image, and the time stamp to a remote electronic device.

24. The method of claim 21, further comprising mounting the temperature assembly on the mobile electronic device such that the tip of the probe is aligned with a field of view of the camera.

25. The method of claim 21, wherein selecting a food product comprises:
    directing the temperature probe towards a container including a food product, whereupon an identifier of the food product is presented on the display identifying the food product; and
    confirming that the identifier is correct before activating the mobile electronic device to acquire the temperature of the selected food product.

26. The method of claim 21, wherein selecting a food product comprises:
    orienting a camera of the mobile electronic device towards a food product, whereupon the mobile electronic device acquires an image of the food product using the camera and analyzes the image and presents an identifier on a display of the mobile electronic device identifying the food product; and
    confirming, by the user, that the identifier identifies the correct selected food product before activating the mobile electronic device to acquire the temperature of the selected food product.

27. The method of claim 26, further comprising presenting an acceptable temperature range for the food product on the display.

28. The method of claim 26, wherein the acceptable temperature range is based on the type of food product.

29. The method of claim 21, further comprising associating a time stamp with the temperature and image of the food product to identify when the temperature and image were acquired.

30. The method of claim 21, wherein the camera is mounted on a back surface of the mobile electronic device opposite the display, the method further comprising mounting the temperature assembly on the back surface of the mobile electronic device such that the tip of the probe is disposed within the field of view of the camera.

31. A method for acquiring temperature data of food products, comprising:
    providing a mobile electronic device including a camera, and a temperature assembly coupled to the mobile electronic device including an elongate probe mounted to the temperature assembly such that a tip of the probe is disposed within a field of view of the camera;
    orienting the camera towards an intended food product, whereupon the mobile electronic device automatically identifies the intended food product based on one or more images from the camera and prompts the user to confirm that the identified food product is the intended food product;
    confirming that the mobile electronic device has identified the correct intended food product;
    inserting the probe into the intended food product; and
    activating the mobile electronic device to acquire a temperature of the intended food product using the temperature sensor and substantially simultaneously acquire an image of the intended food product using the camera.

32. The method of claim 31, wherein, after acquiring the temperature of the intended food product, presenting one or more remedial actions on the display if the temperature is outside an accepted range.

33. The method of claim 31, wherein the elongate probe has a substantially fixed shape such that the tip lies within the field of the view of the camera.

34. The method of claim 31, further comprising presenting an acceptable temperature range for the food product on the display.

35. The method of claim 31, wherein the acceptable temperature range is based on the type of food product.

36. A system for logging temperatures of food products at a physical location, comprising:
    a mobile electronic device including a camera; and
    a temperature assembly including a housing carried by the mobile electronic device, and an elongate temperature probe coupled to the housing and having a substantially fixed shape such that the tip lies within the field of the view of the camera;
    the mobile electronic device comprising a processor configured to acquire a temperature reading from the temperature probe and an image from the camera when a temperature reading is acquired, and memory for storing the temperature reading and image.

* * * * *